US008980599B2

(12) United States Patent  
Tolan et al.

(10) Patent No.: US 8,980,599 B2  
(45) Date of Patent: Mar. 17, 2015

(54) METHOD FOR THE PRODUCTION OF ALCOHOL FROM A PRETREATED LIGNOCELLULOSIC FEEDSTOCK

(75) Inventors: Jeffrey S. Tolan, Ontario (CA); Brian Foody, Ontario (CA); Stephen Rowland, Quebec (CA)

(73) Assignee: Iogen Energy Corporation, Ontario (CA)

( * ) Notice: Subject to any disclaimer, the term of this patent is extended or adjusted under 35 U.S.C. 154(b) by 0 days.

(21) Appl. No.: 12/181,358

(22) Filed: Jul. 29, 2008

(65) Prior Publication Data

US 2009/0035826 A1 Feb. 5, 2009

Related U.S. Application Data

(60) Provisional application No. 60/953,547, filed on Aug. 2, 2007.

(51) Int. Cl.
| | |
|---|---|
| *C12P 7/10* | (2006.01) |
| *C12P 19/14* | (2006.01) |
| *C12P 7/02* | (2006.01) |
| *C12P 7/06* | (2006.01) |
| *C12P 7/08* | (2006.01) |
| *C07K 14/00* | (2006.01) |
| *C07H 3/02* | (2006.01) |
| *B01D 3/00* | (2006.01) |
| *C08H 8/00* | (2010.01) |
| *C12P 19/02* | (2006.01) |
| *C13K 1/02* | (2006.01) |
| *C07K 14/195* | (2006.01) |

(52) U.S. Cl.
CPC ............. *C07H 3/02* (2013.01); *C07K 14/195* (2013.01); *B01D 3/001* (2013.01); *C08H 8/00* (2013.01); *C12P 7/10* (2013.01); *C12P 19/02* (2013.01); *C13K 1/02* (2013.01); *Y02E 50/16* (2013.01)
USPC ............. 435/165; 435/99; 435/155; 435/161; 435/163; 530/350

(58) Field of Classification Search
CPC ............ B01D 3/001; C07H 3/02; C08H 8/00; C12P 7/10; C12P 19/02; C13K 1/02; Y02E 50/16; C07K 14/195
USPC ............. 435/165, 99, 155, 161, 163; 530/350
See application file for complete search history.

(56) References Cited

U.S. PATENT DOCUMENTS

| | | | |
|---|---|---|---|
| 2,529,131 A | 11/1950 | Boinot et al. | |
| 3,032,481 A * | 5/1962 | Harding et al. | 203/24 |
| 4,009,075 A * | 2/1977 | Hoge | 435/162 |
| 4,220,721 A | 9/1980 | Emert et al. | |
| 4,316,956 A | 2/1982 | Lutzen | |
| 4,321,328 A | 3/1982 | Hoge | |
| 4,326,032 A * | 4/1982 | Grove | 435/148 |
| 4,421,856 A | 12/1983 | Muller et al. | |
| 4,447,535 A | 5/1984 | Zucker et al. | |
| 4,460,687 A | 7/1984 | Ehnstrom | |
| 4,497,896 A | 2/1985 | Assarsson et al. | |
| 4,578,353 A | 3/1986 | Assarsson et al. | |
| 4,649,133 A * | 3/1987 | Yoshikumi et al. | 514/42 |
| 4,795,101 A | 1/1989 | Silver | |
| 4,952,504 A | 8/1990 | Pavilon | |
| 5,066,218 A | 11/1991 | Silver | |
| 5,221,357 A | 6/1993 | Brink | |
| 5,487,989 A | 1/1996 | Fowler et al. | |
| 5,554,520 A | 9/1996 | Fowler et al. | |
| 7,070,967 B2 | 7/2006 | Dale et al. | |

FOREIGN PATENT DOCUMENTS

| | | |
|---|---|---|
| CA | 1333367 | 12/1994 |
| CN | 1091774 | 9/1994 |
| EP | 1 836 181 B1 | 3/2009 |
| WO | 86/03514 | 6/1986 |
| WO | 94/06924 | 3/1994 |
| WO | WO2005/099854 A1 * | 10/2005 |

OTHER PUBLICATIONS

Alkasrawi et al., 2002, Applied Biochemistry and Biotechnology, vols. 98-100, p. 849-861.*
Lin, et al., "Ethanol fermentation from biomass resources: current state and prospects", Appl. Microbiol Biotechnol, vol. 69 (2006) 627-42.
Howell, "Enzyme Deactivation during Cellulose Hydrolysis", Biotechnology and Bioengineering vol. XX (1978) 847-63.
Sun, et al., "Hydrolysis of lignocellulosic materials for ethanol production: a review", Bioresource Technology, vol. 83 (2002) 1-11.
Mansfield, et al., "Substrate and Enzyme Characteristics that Limit Cellulose Hydrolysis", Biotechnol. Prog., vol. 15, No. 5 (1999) 804-16.

(Continued)

*Primary Examiner* — Shin Lin Chen
(74) *Attorney, Agent, or Firm* — Fitzpatrick, Cella, Harper & Scinto

(57) ABSTRACT

A process for the production of glucose from a pretreated lignocellulosic feedstock is provided. The method comprises enzymatically hydrolyzing the pretreated lignocellulosic feedstock with cellulase enzymes to produce a hydrolyzate slurry comprising glucose and unhydrolyzed cellulose and fermenting the hydrolyzate slurry in a fermentation reaction to produce a fermentation broth comprising alcohol. A process stream is obtained comprising unhydrolyzed cellulose, which is then subjected to a denaturing step, preferably comprising exposing the unhydrolyzed cellulose to elevated temperatures, thereby producing a heat-treated stream comprising the unhydrolyzed cellulose. The heat-treated stream comprising unhydrolyzed cellulose is then further hydrolyzed with cellulase enzymes to hydrolyze the cellulose to glucose.

18 Claims, 7 Drawing Sheets

(56) References Cited

OTHER PUBLICATIONS

Taherzadeh, et al., "Enzyme-Based Hydrolysis Processes for Ethanol from Lignocellulosic Materials : A Review", BioResources, vol. 2, No. 4 (2007) 707-38.

Stenberg, "Ethanol from Softwood Process Development Based on Steam Pretreatment and SSF", Chemical Engineering 1, Lund University Doctoral Dissertation (1999).

Alkasrawi, et al., "Recirculation of Process Streams in Fuel Ethanol Production from Softwood Based on Simultaneous Saccharification and Fermentation", Applied Biochemistry and Biotechnology, vol. 98-100 (2002) 849-61.

Knutsen, et al., "Combined Sedimentation and Filtration Process for Cellulase Recovery During Hydrolysis of Lignocellulosic Biomass", Applied Biochemistry and Biotechnology, vol. 98-100 (2002) 1161-73.

Mores, et al., "Cellulase Recovery via Membrane Filtration", Applied Biochemistry and Biotechnology, vol. 91-93 (2001) 297-309.

Ramos, et al., "The use of enzyme recycling and the influence of sugar accumulation on cellulose hydrolysis by Trichoderma Cellulases", Enzyme Microb. Technol., vol. 15 (1993) 19-25.

Lee, et al., "Evaluation of Cellulase Recycling Strategies for the Hydrolysis of Lignocellulosic Substrates", Biotechnology and Bioengineering, vol. 45 (1995) 328-36.

Yang et al., "Changes in the Enzymatic Hydrolysis Rate of Avicel Cellulose With Conversion", Biotechnology and Bioengineering, vol. 94, No. 6 (2006) 1122-28.

Desai et al., "Substrate Reactivity as a Function of the Extent of Reaction in the Enzymatic Hydrolysis of Lignocellulose", Biotechnology and Bioengineering, vol. 56, No. 6 (1997) 650-55.

\* cited by examiner

METHOD FOR THE PRODUCTION OF ALCOHOL FROM A PRETREATED LIGNOCELLULOSIC FEEDSTOCK

RELATED APPLICATIONS

This application claims the priority benefit of a provisional application entitled Method For the Production of Alcohol From a Pretreated Lignocellulosic Feedstock, Ser. No. 60/953,547, filed Aug. 2, 2007, the entire contents of which are incorporated herein by reference.

FIELD OF INVENTION

The present invention relates to an improved method for the production of fermentable sugar from a lignocellulosic feedstock. More specifically, the present invention relates to the production of glucose from a lignocellulosic feedstock and its subsequent conversion to a fermentation product.

BACKGROUND OF THE INVENTION

Fuel ethanol is currently produced from feedstocks such as corn starch, sugar cane, and sugar beets. However, the production of ethanol from lignocellulose-containing feedstocks, such as agricultural wastes and forestry wastes has received much attention in recent years. An advantage of using these feedstocks is that they are widely available and can be obtained at low cost. In addition, lignocellulosic feedstocks are typically burned or landfilled, and thus using these feedstocks for ethanol production offers an attractive alternative to disposing of them. Yet another advantage of these feedstocks is that a byproduct of the conversion process, known as lignin, can be used as a fuel to power the process instead of fossil fuels. Several studies have concluded that, when the entire production and consumption cycle is taken into account, the use of ethanol produced from cellulose generates close to nil greenhouse gases.

The first chemical processing step for converting lignocellulosic feedstock to ethanol, or other fermentation products, involves breaking down the fibrous material to liberate sugar monomers, such as glucose, from the feedstock for conversion to ethanol in a subsequent step of fermentation. The two primary processes are acid or alkali hydrolysis, which involve the hydrolysis of the feedstock using a single step of chemical treatment, and enzymatic hydrolysis, which involves an acid or alkali pretreatment followed by hydrolysis with cellulase enzymes.

In the acid or alkali hydrolysis process, the raw material is contacted with a strong acid or alkali under conditions sufficient to hydrolyze the cellulose to glucose and hemicellulose to xylose and arabinose. The glucose is then fermented to ethanol using yeast, and the ethanol is recovered and purified by distillation. Although this process produces ethanol, the yield is low due to the non-selective nature of the acid or alkaline hydrolysis.

In the enzymatic hydrolysis process, the lignocellulosic feedstock is first subjected to a pretreatment under conditions which are milder than that in the acid or alkali hydrolysis process. The purpose of the pretreatment is to increase the cellulose surface area and convert the fibrous feedstock to a muddy texture, with limited conversion of the cellulose to glucose. The cellulose is then hydrolyzed to glucose in a subsequent step that uses cellulase enzymes. Prior to the addition of enzyme, the pH of the pretreated feedstock is adjusted to a value that is amenable for the enzymatic hydrolysis reaction. The optimal pH range for cellulases is typically 4 to 6, although the pH can be higher if alkalophilic cellulases are used.

Cellulase is a generic term denoting a multi-enzyme mixture comprising exo-cellobiohydrolases (CBH) and endoglucanases (EG) that catalyze the hydrolysis of the cellulose ($\beta$-1,4-D-glucan linkages). The CBH enzymes, CBHI and CBHII, act on the ends of the glucose polymers in cellulose microfibrils liberating cellobiose, while the EG enzymes act at random locations on the cellulose. Together, cellulase enzymes hydrolyze cellulose to cellobiose, which is then hydrolyzed to glucose by the enzyme $\beta$-glucosidase. Cellulase enzymes hydrolyze cellulose by binding to the substrate by virtue of their cellulose binding domains, while $\beta$-glucosidase enzymes typically lack such a binding domain and thus remain in solution.

It is also known to use cellulase enzymes in starch-conversion processes to improve the yield of starch from the raw material. However, the processing steps to produce glucose from corn, or other feedstocks containing high levels of starch, are different from those employed to produce glucose from lignocellulosic feedstocks. In starch-conversion processes, it is first necessary to separate starch from the raw material. This is carried out by steeping the corn by the application of mild heat and the addition of sulfur dioxide or sulfurous acid, followed by subjecting the steeped feedstock to multiple grinding steps, and separating the starch, protein and other components. The cellulase may be added to the steep liquor or to the subsequent grinding steps to improve the starch yield by hydrolyzing the grain fiber. (See for example Silver, U.S. Pat. Nos. 5,066,218 and 4,795,101). By contrast, in lignocellulosic conversion processes, cellulase enzymes are used to produce glucose from the cellulose component of the feedstock for subsequent fermentation to ethanol.

One factor that decreases the efficiency of the cellulase hydrolysis of lignocellulosic feedstocks to fermentable sugars is that the enzymes are inhibited by glucose. Methods have been proposed to decrease this inhibition by lowering the concentration of glucose in solution during the hydrolysis. One such method, known as "Simultaneous Saccharification and Fermentation" (SSF), involves carrying out the enzymatic hydrolysis concurrently with yeast fermentation of glucose to ethanol in a reactor vessel. By performing both reactions simultaneously, the yeast consumes glucose by fermenting it to ethanol, thereby reducing its concentration in the reactor which, in turn, decreases its inhibitory effect. However, SSF is typically carried out at temperatures of 35-38° C., which is lower than the 50° C. optimum for cellulase and higher than the 28° C. optimum for yeast. This non-ideal temperature range results in substandard performance by both the cellulase enzymes and the yeast. As a result, the hydrolysis requires very long reaction times and very large reaction vessels, both of which are costly.

Another approach which has been proposed to increase the efficiency of the hydrolysis of feedstocks to produce fermentable sugar is to subject unconverted substrate remaining in downstream stages in the process to further hydrolysis, either in upstream or downstream hydrolysis reactions. These processes have been proposed to improve the yield of fermentable sugar obtained from the raw material, thereby increasing the ethanol recovered.

Such processes are disclosed in U.S. Pat. No. 2,529,131 (Boinot et al.) and U.S. Pat. Nos. 4,578,353 and 4,497,896 (Assarsson et al.). In particular, these processes involve subjecting starch-containing feedstocks to acid hydrolysis to produce sugar, followed by fermentation to obtain ethanol and distillation of the ethanol. A residual stream remaining after distillation is subjected to further hydrolysis, which converts the unfermentable products remaining to fermentable sugars. U.S. Pat. No. 2,529,131 discloses further hydrolyzing unfermentable materials remaining after distillation, referred to as "vinasse", in a second hydrolysis, while U.S. Pat. Nos. 4,578,353 and 4,497,896 recycle a stream obtained from a "stillage" stream remaining after distillation as a feedstock to a continuous hydrolyzer. However, each of the above-described methods utilizes acid hydrolysis to produce glucose. Although acid hydrolysis is typically employed for hydrolyzing starch, it is not a suitable method for producing glucose from lignocellulosic feedstock due to the low yields of the sugar obtained.

U.S. Pat. No. 4,447,535 (Zucker et al.) discloses a process for the recovery of a concentrated stillage in the production of alcohol from starch or starch-containing raw materials. According to this process, the starch or starch-containing raw material, in a suitably crushed form, is introduced to a homogenizer together with steam. After gelatinization, the starch is liquified enzymatically, diluted, saccharified enzymatically and then fermented. The product is subsequently distilled to produce alcohol and stillage, followed by separating coarse materials from the stillage. This is followed by recycle of the stillage by mixing it with raw material fed to the process. However, the process of Zucker et al. could not be employed to produce fermentable sugar from a lignocellulosic material since the process steps are directed to hydrolyzing the starch present in the raw material, rather than the cellulosic component.

Furthermore, methods that use starch for ethanol production suffer from the limitation that most of the farmland which is suitable for the production of starch is already in use as a food source for humans and animals. An additional disadvantage of starch conversion processes is that fossil fuels are used in the conversion processes, and for producing the fertilizer required for cultivation of the starch-containing grains. Thus, these processes have only a limited impact on reducing greenhouse gases.

Canadian Patent No. 1,333,367 (Gutschireiter) discloses a method for producing ethanol from sugar-containing raw materials, which first involves extracting the raw material with an aqueous solution with the application of heat to remove soluble sugars, followed by fermenting the extract to produce ethanol. After a step of distillation, a remaining water-enriched stillage stream is recycled in counterflow to the extraction step. However, the disclosure is directed to the production of ethanol from sugar cane, which is not a lignocellulosic material. Similar to starch-containing raw materials, sugar cane is used for human consumption and thus is not a preferred feedstock for ethanol production. In addition, these processes may also require the use of fossil fuels to provide energy for the conversion process.

U.S. Pat. No. 4,421,856 (Muller et al.) discloses a process for producing ethanol by hydrolyzing an aqueous slurry of a carbohydrate polymer selected from starch or cellulose using acid hydrolysis, followed by fermentation and distillation. A stillage stream resulting from the distillation is used as a source of added water soluble carbohydrate fed to the initial hydrolysis. However, the method employs acid hydrolysis, which, as set forth previously, is not a suitable method for hydrolyzing lignocellulosic feedstocks to glucose.

It is also known to re-circulate process streams arising from the conversion of cellulosic feedstocks to ethanol back to upstream hydrolysis reactions. Such processes are disclosed by U.S. Pat. No. 5,221,357 (Brink), U.S. Pat. Nos. 5,554,520 and 5,487,989, (Fowler et al.), U.S. Pat. No. 4,952,504 (Pavilon), Stenberg (PhD thesis, Department of Chemical Engineering 1, Lund University, Sweden) and Alkasrawi et al. (Appl. Biochem. and Biotech., 2002, 98-100:849-861).

U.S. Pat. No. 5,221,357 (supra) discloses a two stage acid hydrolysis of lignocellulosic material. A hydrolyzate resulting from the second stage hydrolysis is subjected to a solids-liquid separation with recycle of the liquid portion to the first stage hydrolysis. The separated solids are sent to a wet oxidation process wherein steam produced by the exothermic oxidation reactions can be used as a source of heat for the process. A disadvantage of this process is that the solids sent to the wet oxidation would comprise unhydrolyzed cellulose. Thus, the process does not make full use of the hydrolysable substrate present in the raw material.

U.S. Pat. Nos. 5,554,520 and 5,487,989 (supra) disclose a process for converting biomass to ethanol which involves breaking down a pretreated biomass into simpler oligosaccharides and/or monosaccharides with polysaccharase in an enzyme hydrolysis reactor, followed by fermentation and distillation to obtain ethanol. A mixture of solids and liquid is drawn from the enzyme hydrolysis reactor and into a solids/liquid separator. Solids are returned to the enzyme reactor, and the effluent sent to fermentation.

The process disclosed by U.S. Pat. No. 4,952,504 (supra) involves hydrolyzing citrus peel by means of a fuel fired heater. The hydrolysis relies on organic acids present within the biomass itself to hydrolyze the hemicellulose and cellulose components of the feedstock. Also disclosed is a method of hydrolyzing wood or other biomass by using carbonic acid produced in the system from carbon dioxide liberated during a fermentation reaction. After hydrolysis, the sugars are fermented to produce ethanol. The fermentation broth containing ethanol is then distilled, with recycle of a portion of the stillage to the raw material. However, this process relies on acid and the application of heat to hydrolyze both the cellulose and hemicellulose components of the biomass, which is subject to the limitations described previously.

Stenberg (supra) discloses the recycling of process streams arising from ethanol production from softwood by pretreatment, cellulase hydrolysis and fermentation, followed by distillation to recover the ethanol. The aim of these studies was to reduce the amount of fresh water required in the process. However, the processes disclosed in Stenberg all employ a filtration step to separate solids prior to recirculation of the process stream. Such filtration steps would remove not only lignin, but also unhydrolyzed cellulose, thus resulting in a loss of fermentable sugar from the process.

In a later related study by the same group, (Alkasrawi et al., supra) the effect of re-circulating the filtered aqueous process streams, described by Stenberg, on ethanol production was investigated. These studies were conducted to investigate the effect of inhibitors present in the recirculation streams on ethanol yield. It was found that at higher degrees of recirculation, fermentation was clearly inhibited, resulting in a decrease in ethanol yield, while hydrolysis seemed unaffected.

Processes involving recycling of streams remaining after distillation back to a fermentation reactor are also known. U.S. Pat. No. 4,460,687 (Ehnstrom) discloses a process for producing ethanol involving recycling stillage back to a fermentor. By this stillage recirculation, the ethanol concentration in the fermentor can be maintained at a desired low value below the limit for ethanol inhibition. Similarly, U.S. Publication No. 2005/0019932 (Dale et al.) discloses a process for producing ethanol from molasses or corn syrup in which stillage is recycled back to the fermentor. In Dale et al., the recycling step is employed to reduce the amount of stillage sent to waste treatment. However, neither of these processes are directed to improving the efficiency of the enzymatic conversion of the raw material to fermentable sugars.

Another significant problem with the enzymatic hydrolysis of lignocellulosic feedstocks is the large amount of cellulase enzyme required. This is a major shortcoming of the process since the cellulase accounts for more than 50% of the cost of hydrolysis. Although the enzyme dosage can be reduced by increasing the hydrolysis times (90-200 hours), this requires very large reactors, which again adds to the overall cost. By increasing the efficiency of the enzyme hydrolysis, it would be possible to reduce enzyme dosage.

In this connection, it has been proposed to recover the cellulase enzymes and reuse them in further hydrolysis reactions. Known methods for reusing enzyme rely on the binding of the enzyme to unconverted cellulose or by the addition of fresh cellulose. The cellulose, which contains bound enzyme, is then sent back to the hydrolysis reactor. Such a process is disclosed by U.S. Pat. No. 4,321,328 (Hoge). According to this process, a cellulosic material is mechanically defibered and then saccharified to form fermentable sugars, followed by fermentation to produce an ethanol-containing beer. The ethanol-containing beer is then recycled to the hydrolysis reaction, along with enzymes that bind to unreacted cellulosic material in the beer.

Knutsen and Davis (Appl. Biochem. Biotech., 2002, 98-100:1161-1172) disclose a combined inclined sedimentation and ultrafiltration process for recovering cellulase enzymes during the hydrolysis of lignocellulosic biomass. The process first involves hydrolyzing lignocellulosic particles with cellulase enzymes and then feeding the resulting mixture into an inclined settler. Large lignocellulosic particles, including enzyme bound to the particles, are retained in the inclined settler and returned to the reactor with the settler underflow. The overflow is then fed to a crossflow ultrafiltration unit to recover unbound cellulases, which are then added back to the hydrolysis reactor.

Likewise, Mores et al. (Appl. Biochem. Biotech., 2001, 91-93:297-309) disclose a combined inclined sedimentation and ultrafiltration process similar to that described by Knutsen and Davis (supra), although the process of Mores et al. involves an extra clarification step involving subjecting the settler overflow to microfiltration prior to ultrafiltration to reduce fouling of the ultrafiltration membrane. However, a disadvantage of the processes of Knutsen and Davis and Mores et al. (supra) is that incorporating a settler in a commercial-scale hydrolysis reactor would add significant cost and complexity.

Ramos et al. (Enzyme Microb. Technol., 1993, 15:19-25) disclose a process in which steam-exploded eucalyptus chips are hydrolyzed using cellulase with removal of soluble sugars and the recycling of enzyme. The process involves terminating the reaction at selected incubation times, collecting the unhydrolyzed, enzyme-containing residue on a sintered glass filter, and washing the enzyme-containing residue with hydrolysis buffer to remove soluble sugars. The washed residue is then re-suspended in fresh hydrolysis buffer containing fresh β-glucosidase enzyme and hydrolyzed. A similar process is disclosed by Lee et al. (Biotech. Bioeng., 1994, 45:328-336).

U.S. Pat. No. 4,316,956 (Lützen) discloses the production of ethanol from starch by the addition of glucoamylase and alpha-amylase to granular starch concurrently with yeast to a fermentor, followed by steam stripping of the resulting fermentation broth to recover the ethanol. The method involves recycle of some of the stillage, which contains the alpha-amylase and a minor portion of the glucoamylase, back to the fermentor. However, recycling of the amylase enzymes present in the still bottoms back to fermentation requires that they be heat labile to withstand the high temperatures of steam stripping, or requires care to avoid subjecting the fermentation broth to temperatures that deactivate the enzyme.

U.S. Pat. No. 4,220,721 (Emert et al.) discloses a simultaneous saccharification and fermentation (SSF) process in which EG and CBH cellulase enzyme components are recycled. The process involves separating a liquid fraction from the SSF reaction mixture, followed by contacting the liquid fraction and the enzyme with a cellulose-containing solid to adsorb the enzymes thereon. The solid fraction containing the adsorbed enzymes is then separated and used as a portion of the feed to a further SSF reaction. However, a disadvantage of this process is that it requires the addition of fresh cellulose substrate to bind the enzyme, which increases the cost and complexity of the process.

Thus, at present, there is much difficulty in the art to operate an efficient process for hydrolyzing lignocellulosic feedstocks to produce a high yield of fermentable sugar. Known methods that involve further hydrolysis of unconverted substrate or recycling of enzyme are subject to the limitations set forth above. The development of an efficient process remains a critical requirement to convert cellulose to a fermentation product, such as ethanol.

SUMMARY OF THE INVENTION

The present invention relates to an improved method for the production of fermentable sugar from a lignocellulosic feedstock. More specifically, the present invention relates to the production of glucose from a lignocellulosic feedstock and its subsequent conversion to a fermentation product.

The present invention overcomes several disadvantages of the prior art by taking into account the difficulties encountered in steps carried out during the conversion of a lignocellulosic feedstock to an alcohol, such as ethanol. In the present invention, the inventors have provided methods for increasing the amount of fermentable sugar obtained from a lignocellulosic feedstock. Advantageously, by increasing the yield of fermentable sugar(s) from the lignocellulosic feedstock, the amount of alcohol, or other fermentation products, produced by the process can be significantly improved.

In particular, the invention is based on the surprising finding that unhydrolyzed cellulose remaining after cellulase hydrolysis of a pretreated feedstock is particularly amenable to further hydrolysis by cellulases if the unhydrolyzed cellulose is previously exposed to an enzyme denaturation step including exposing the unhydrolyzed cellulose to changes in pH, protease treatment, the addition of oxidizing chemicals, or other chemicals that inactivate enzyme. Without wishing to be bound by theory, it is believed that the enhancements in cellulase hydrolysis observed may be due to denaturation of bound enzyme, thereby regenerating the surface of the cellulose. This, in turn, increases the sites on the substrate surface available for further hydrolysis by the cellulase enzymes.

Thus, according to a broad aspect of the present invention, a process stream comprising unhydrolyzed cellulose resulting from a previous pretreatment and cellulase hydrolysis of a lignocellulosic feedstock is subjected to a processing step comprising exposing the unhydrolyzed cellulose in the process stream to conditions which denature bound cellulase enzyme and hydrolyzing that unhydrolyzed cellulose which has been exposed to such denaturing conditions to glucose by further hydrolysis with cellulase enzymes.

The process stream comprising unhydrolyzed cellulose may arise from various stages in the processing of the lignocellulosic feedstock to alcohol. According to one embodiment of the invention, the process stream is a fermentation broth arising from pretreatment of a lignocellulosic feedstock followed by cellulase enzyme hydrolysis to produce glucose and fermentation of the glucose to alcohol. The fermentation broth obtained in this manner is then distilled to obtain concentrated alcohol and a still bottoms stream, followed by subjecting the still bottoms stream to further cellulase hydrolysis. Since the temperatures of the distillation step are harsh enough to denature bound cellulase enzyme remaining from the enzyme hydrolysis, the unhydrolyzed cellulose remaining in the still bottoms stream can be efficiently hydrolyzed to glucose. Alternatively, the fermentation broth may be subjected to a heat treatment involving the direct application of heat to the stream, followed by the step of further hydrolysis with cellulases.

According to another embodiment of the invention, the process stream is a hydrolyzate slurry comprising glucose resulting from a pre-treatment and cellulase hydrolysis of a lignocellulosic feedstock. By subjecting this process stream to a processing step involving a heat treatment, cellulase enzyme which is bound to the unhydrolyzed cellulose is denatured. The heat-treated hydrolyzate slurry is then further hydrolyzed with cellulase enzymes with improved efficiency.

The further cellulase hydrolysis may comprise recycling the heat-treated stream to an upstream hydrolysis or to a downstream hydrolysis with the addition of fresh cellulase.

DESCRIPTION OF THE DRAWINGS

In the accompanying drawings:

In FIG. 1 a still bottoms stream is fed to downstream cellulose hydrolysis, in FIG. 2, the still bottoms stream is recycled to an upstream cellulose hydrolysis, in FIG. 3, a fermentation broth is fed to an upstream cellulose hydrolysis and in FIG. 4 a hydrolyzate slurry resulting from a cellulose hydrolysis is recycled back to an upstream cellulase hydrolysis.

In FIG. 5, 3 mg/g of cellulase was added at the beginning of the hydrolysis and the wheat straw slurry contained 2.53% cellulose. Yeast was added at a concentration of 1.5 g/L at the start of the fermentation, and the simulated distillation was conducted at 72 hours from addition of cellulase enzymes. Fresh cellulase enzyme at a dose of 30 mg/g was added, after the simulated distillation. In FIG. 6, cellulase was added at 30 mg/g at the beginning of the hydrolysis and the wheat straw slurry contained 6.01% cellulose. Yeast was added at a concentration of 1.5 g/L at 24 hours and simulated distillation was conducted at 48 hours. After simulated distillation, 30 mg/g of fresh enzyme was added.

DETAILED DESCRIPTION

Figure 1:
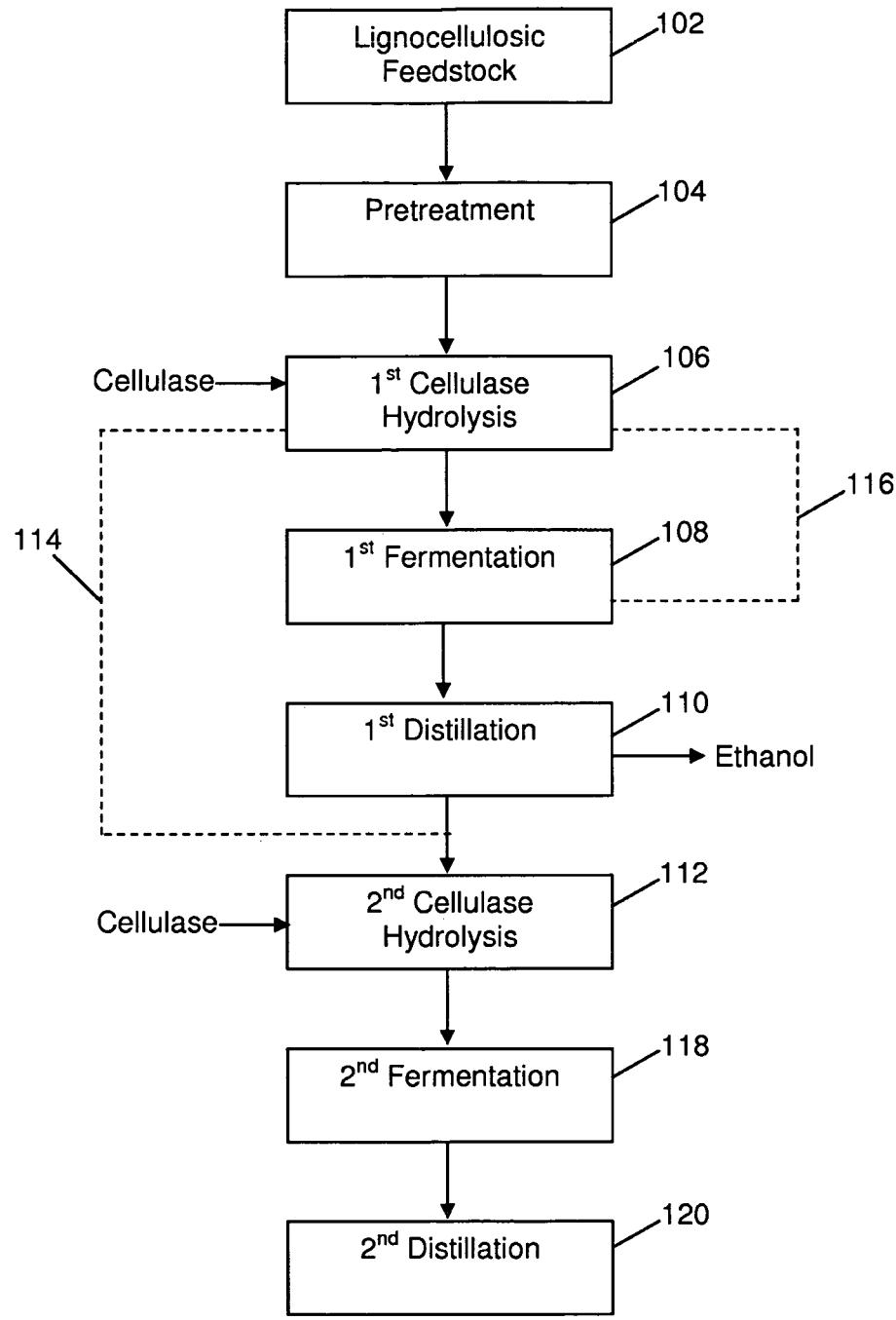
FIGS. 1, 2, 3, and 4 are process flow diagrams depicting pretreatment of a lignocellulosic feedstock, followed by cellulose hydrolysis, fermentation, distillation and further hydrolysis of various streams obtained from the process comprising unhydrolyzed cellulose.

The following description is of an embodiment by way of example only and without limitation to the combination of features necessary for carrying various aspects of the present invention into effect.

The feedstock for the process of the present invention is a lignocellulosic material. By the term "lignocellulosic feedstock" is meant any type of plant biomass such as, but not limited to, non-woody plant biomass, cultivated crops such as, but not limited to grasses, for example, but not limited to, $C_4$ grasses, such as switch grass, cord grass, rye grass, miscanthus, reed canary grass, or a combination thereof, sugar processing residues, for example, but not limited to bagasse, beet pulp, or a combination thereof, agricultural residues, for example, but not limited to, soybean stover, corn stover, rice straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, or fully dried lignocellulosic feedstock.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. The lignocellulosic feedstock also comprises lignin in an amount greater than about 10%, more typically in an amount greater than about 15% (w/w). The lignocellulosic feedstock may also comprise small amounts of sucrose, fructose and starch.

Examples of preferred lignocellulosic feedstocks include (1) agricultural wastes such as corn stover, wheat straw, barley straw, canola straw, oat straw, rice straw and soybean stover; and (2) grasses such as switch grass, miscanthus, cord grass and reed canary grass.

The present invention is generally practiced with a lignocellulosic material that has been pretreated. Pretreatment methods are intended to deliver a sufficient combination of mechanical and chemical action so as to disrupt the fiber structure and increase the surface area of feedstock to make it accessible to cellulase enzymes. Mechanical action typically includes the use of pressure, grinding, milling, agitation, shredding, compression/expansion and chemical action includes the use of heat (often steam), acid or alkali, or solvents.

The pretreatment is preferably a chemical treatment involving the addition of a pH alterant which alters the pH of the feedstock to disrupt its fiber structure and increase its accessibility to being hydrolyzed in a subsequent enzymatic hydrolysis.

In one embodiment of the invention, the pH alterant is an acid. Pretreatment with acid hydrolyzes the hemicellulose, or a portion thereof, that is present in the lignocellulosic feedstock to the monomeric sugars xylose, arabinose, mannose, galactose, or a combination thereof. Preferably, the acid pretreatment is performed so that nearly complete hydrolysis of the hemicellulose and a small amount of conversion of cellulose to glucose occurs. The cellulose is hydrolyzed to glucose in a subsequent step that uses cellulase enzymes. Typically a dilute acid, at a concentration from about 0.02% (w/w) to about 2% (w/w), or any amount therebetween, (measured as the percentage weight of pure acid in the total weight of dry feedstock plus aqueous solution) is employed for the pretreatment. Preferably, the acid pretreatment is carried out at a peak temperature of about 180° C. to about 250° C. for a time of about 6 seconds to about 600 seconds, at a pH of about 0.8 to about 2.0. It should be understood that the acid pretreatment may be carried out in more than one stage, although it is preferably performed in a single stage.

In an embodiment of the invention, the acid pretreatment is performed at a peak temperature, in ° C. of about of 180, 190, 200, 210, 220, 230, 240 or 250. In a further embodiment of the invention, the duration of the pretreatment is, in seconds, of about 6, 50, 100, 150, 200, 250, 300, 350, 400, 450, 500, 450, 500, 550 or 600. In yet a further embodiment, the pH of the feedstock during pretreatment is about 0.8, 1.0, 1.2, 1.4, 1.6, 1.8 or 2.0.

One method of performing acid pretreatment of the feedstock is steam explosion, using the process conditions described in U.S. Pat. No. 4,461,648 (Foody). The pretreatment may be a continuous process as disclosed in U.S. Pat. No. 5,536,325 (Brink); co-pending U.S. Application Ser. No. 60/687,224 (Foody and Tolan); and U.S. Pat. No. 4,237,226 (Grethlein). Other techniques that are known in the art and that may be used as required, include, but are not limited to, those disclosed in U.S. Pat. No. 4,556,430 (Converse et al.).

In another embodiment of the invention, the pH alterant used for pretreatment of the lignocellulosic feedstock is alkali. In contrast to acid pretreatment, pretreatment with alkali does not hydrolyze the hemicellulose component of the feedstock, but rather the alkali reacts with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. The pretreatment is preferably not conducted with alkali that is insoluble in water, such as lime and magnesium hydroxide.

An example of a suitable alkali pretreatment is Ammonia Freeze Explosion, Ammonia Fiber Explosion or Ammonia Fiber Expansion ("AFEX" process). According to this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See, for example, U.S. Pat. Nos. 5,171,592, 5,037,663, 4,600,590, 6,106,888, 4,356,196, 5,939,544, 6,176,176, 5,037,663 and 5,171,592). The flashed ammonia may then be recovered according to known processes. Another alkali pretreatment is with low ammonia concentrations (See, for example, US Application Publication No 20070031918 and US Application Publication No 20070037259).

After the pretreatment, the lignocellulosic feedstock may be treated to obtain a solids stream comprising the pretreated feedstock and an aqueous stream comprising soluble components. This may be carried out by washing the pretreated feedstock with an aqueous solution to produce a wash stream, and a solids stream comprising the pretreated feedstock. This may be carried out by subjecting the pretreated feedstock to solids-liquid separation, using known methods such as centrifugation, microfiltration, plate and frame filtration, cross-flow filtration, pressure filtration, vacuum filtration and the like. Optionally, a washing step may be incorporated into the solids-liquids separation. When an acidic pretreatment is employed, the aqueous phase comprises sugars produced by the hydrolysis of hemicellulose, as well as the acid added during the pretreatment and any organic acids liberated during the pretreatment. This stream may be subsequently processed to remove the mineral acid and organic acid, and then optionally fed back to the solids stream comprising the pretreated feedstock. The aqueous stream obtained from the acid pretreated feedstock may also be subjected to a fermentation to ferment the sugars. For example, xylose present in this stream may be fermented to ethanol, xylitol, lactic acid, butanol, or a mixture thereof.

The pretreated lignocellulosic feedstock is typically slurried in an aqueous solution such as process water, fresh water, steam condensate or process recycle streams. The concentration of pretreated lignocellulosic feedstock in the slurry depends on the particle size, water retention, pump capacity and other properties of the feedstock. Typically, the concentration is between about 3% and 30% (w/w), or between about 10% and about 20% (w/w) fiber solids (also known as suspended or undissolved solids), or any amount therebetween. The aqueous slurry preferably has a solids concentration that enables it to be pumped. As is well known in the art, the concentration of suspended or undissolved solids can be determined by filtering a sample of the slurry using glass microfiber filter paper, washing the filter cake with water, and drying the cake overnight at 105° C. It is preferred that the fiber solids comprise at least about 20% to about 70% cellulose by weight, or any amount therebetween. For example, the fiber solids may comprise, in %, about 20, 25, 30, 35, 40, 45, 50, 55, 60, 65 or 70 cellulose.

The pH of the pretreated feedstock is typically adjusted to a value that is optimal for the cellulase enzymes used. Generally, the pH of the pretreated feedstock is adjusted to within a range of about 3.0 to about 7.0, or any pH therebetween. Preferably, the pH is within a range of about 4.0 to about 6.0, more preferably between about 4.5 and about 5.5. If the pretreated feedstock is alkaline (i.e., if an alkali pretreatment is performed), sulfuric acid may be used for the pH adjustment. If the pretreated feedstock is acidic, the pH may be adjusted with alkali selected from the group consisting of ammonia, ammonium hydroxide, lime, calcium hydroxide, potassium hydroxide, magnesium hydroxide and sodium hydroxide. Preferably, the alkali is selected from the group consisting of ammonia, ammonium hydroxide and sodium hydroxide.

The temperature of the pretreated feedstock is adjusted so that it is within the optimum range for the activity of the cellulase enzymes. Generally, a temperature of about 45° C. to about 55° C., or any temperature therebetween, e.g. 46° C., 47° C., 48° C., 49° C., 50° C., 51° C., 52° C., 53° C., and 54° C. is suitable for most cellulase enzymes. Thermophilic cellulases are effective at temperatures of 55° C. to 70° C.

The cellulase enzymes and the β-glucosidase enzyme are added to the pretreated feedstock, prior to, during, or after the adjustment of the temperature and pH of the aqueous slurry after pretreatment. Preferably the cellulase enzymes and the β-glucosidase enzyme are added to the pretreated lignocellulosic feedstock after the adjustment of the temperature and pH of the slurry.

By the term "cellulase enzymes" or "cellulases," it is meant a mixture of enzymes that hydrolyze cellulose. The mixture may include glucobiohydrolases (GBH), cellobiohydrolases (CBH) and endoglucanases (EG). Although GBH enzymes may form a component of the enzyme mixture, their use in the enzymatic hydrolysis of cellulose is less common than CBH and EG enzymes. In a non-limiting example, the mixture includes CBH and EG enzymes. The GBH enzyme primarily hydrolyzes cellulose polymer chains from their ends to release glucose, while the CBH enzyme primarily hydrolyzes cellulose polymer chains from their ends to release cellobiose and the EG enzyme primarily hydrolyzes cellulose polymer in the middle of the chain.

The process of the present invention can be carried out with any type of cellulase enzymes, regardless of their source. Examples of cellulases that may be used in the practice of the invention include those obtained from fungi of the genera *Aspergillus, Humicola*, and *Trichoderma*, and from bacteria of the genera *Bacillus* and *Thermobifida*.

An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268).

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC #3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. The preferred β-glucosidase enzyme for use in this invention is the Bgl1 protein from *Trichoderma reesei*. It is also contemplated that the β-glucosidase enzyme may be modified to include a cellulose binding domain, thereby allowing this enzyme to bind to cellulose.

The cellulase enzymes and β-glucosidase enzymes may be handled in an aqueous solution or as a powder or granulate. The enzymes may be added to the pretreated feedstock at any point prior to its introduction into a hydrolysis reactor. Alternatively, the enzymes may be added directly to the hydrolysis reactor, although addition of enzymes prior to their introduction into the hydrolysis reactor is preferred for optimal mixing. The enzymes may be mixed into the pretreated feedstock using mixing equipment that is familiar to those of skill in the art.

In practice, the hydrolysis is carried out in a hydrolysis system, which includes a series of hydrolysis reactors. The number of hydrolysis reactors in the system depends on the cost of the reactors, the volume of the aqueous slurry, and other factors. For a commercial-scale ethanol plant, the typical number of hydrolysis reactors is 4 to 12. In order to maintain the desired hydrolysis temperature, the hydrolysis reactors may be jacketed with steam, hot water, or other heat sources. Preferably, the cellulase hydrolysis is a continuous process, with continuous feeding of pretreated lignocellulosic feedstock and withdrawal of the hydrolyzate slurry. However, it should be understood that batch processes are also included within the scope of the present invention.

Other design parameters of the hydrolysis system may be adjusted as required. For example, the volume of a hydrolysis reactor in a cellulase hydrolysis system can range from about 100,000 L to about 3,000,000 L, preferably between 200,000 and 750,000 L, although reactors of small volume are preferred to reduce cost. The total residence time of the slurry in a hydrolysis system may be between about 12 hours to about 200 hours, preferably 25 to 100 hours. The hydrolysis reactors may be unmixed or subjected to light agitation, typically with a maximum power input of up to 0.8 hp/1000 gallons.

The enzymatic hydrolysis with cellulase enzymes produces a hydrolyzate slurry comprising glucose, unhydrolyzed cellulose and lignin. Other components that may be present in the hydrolyzate slurry include the sugars xylose, arabinose, mannose and galactose, as well as silica, insoluble salts and other compounds.

The hydrolyzate slurry may be subjected to a heat treatment conducted at temperatures of between 70° C. and 200° C., more preferably between 90 and 180° C. to denature bound cellulase enzyme, followed by a further hydrolysis with cellulase enzymes. The further hydrolysis may involve introducing the heat-treated hydrolyzate slurry to either an upstream or a downstream hydrolysis with cellulase. In one embodiment of the invention, the hydrolyzate slurry is exposed to a temperature, in ° C. of 70, 80, 90, 100, 110, 120, 130, 140, 150, 160, 170, 180, 190 or 200 prior to further hydrolysis. The retention time of the hydrolyzate slurry in the heat treatment may be between 30 seconds and 24 hours and will depend on the temperature of the heat treatment, with longer retention times typically being required when lower temperatures are employed. In various embodiments of the present invention, the retention time is about 30 seconds, about 1 min., about 10 min., about 20 min., about 30 min., about 1 hour, about 2 hours, about 3 hours, about 5 hours, about 8 hours, about 10 hours, about 15 hours, about 20 hours or about 24 hours. The heat treatment is preferably conducted at a pH of between about 3 and about 9; for example, the pH may be about 3, about 4, about 5, about 6, about 7, about 8 or about 9.

Sugars present in the hydrolyzate slurry are then fermented by microbes to produce a fermentation broth comprising an alcohol. For ethanol production, the fermentation is typically carried out with a *Saccharomyces* spp. yeast. Preferably, glucose and any other hexoses typically present in the hydrolyzate slurry are fermented to ethanol by wild-type *Saccharomyces cerevisiae*, although genetically modified yeasts may be employed as well. For example, the fermentation may be performed with a recombinant *Saccharomyces* yeast that is engineered to ferment both hexose and pentose sugars to ethanol. Recombinant yeasts that can ferment the pentose sugar, xylose, to ethanol are described in U.S. Pat. No. 5,789,210, the entire contents of which are herein incorporated by reference. Furthermore, the pentose sugars, arabinose and xylose, may be converted to ethanol by the yeasts described in Boles et al. (WO 2006/096130).

Examples of other fermentation products included within the scope of the invention include sorbitol, butanol, 1,3-propanediol and 2,3-butanediol. Other microorganisms that may be employed in the fermentation include wild-type or recombinant *Escherichia, Zymomonas, Candida, Pichia, Streptomyces, Bacillus, Lactobacillus* and *Clostridium*.

Preferably, the fermentation is performed at or near the temperature and pH optima of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The pH of a typical fermentation employing *Saccharomyces cerevisiae* is between about 3 and about 6. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The hydrolyzate slurry may also be supplemented with additional nutrients required for growth of the fermentation microorganism. For example, yeast extract, specific amino acids, phosphate, nitrogen sources, salts, trace elements and vitamins may be added to the hydrolyzate slurry to support growth of the microorganism.

The fermentation may be conducted in batch, continuous or fed-batch modes with or without agitation. Preferably, the fermentation reactors are agitated lightly with mechanical agitation. A typical commercial-scale fermentation may be conducted using a series of reactors, such as, for example, 1 to 6. The fermentation microorganisms may be recycled back to the fermentor or may be sent to distillation without recycle.

It should be understood that the hydrolysis and fermentation reactions can be conducted simultaneously in the same reactor, although it is preferred that the hydrolysis and fermentation are performed separately to achieve optimal temperature conditions for each reaction.

The fermentation broth comprising the alcohol may then be subjected to a heat treatment to denature bound cellulase enzyme. The heat treatment may be part of a distillation operation conducted to separate the alcohol from the fermentation broth or "beer", as described in more detail below. Alternatively, the heat treatment may be carried out by the direct application of heat to the fermentation broth. In the latter case, the fermentation broth is subjected to temperatures of between about 70 and about 200° C., more preferably between about 90 and about 180° C. The retention time of the heat treatment may be between about 30 seconds and about 24 hours. In one embodiment of the invention, the fermentation broth is exposed to a temperature, in ° C., of about 70, about 80, about 90, about 100, about 110, about 120, about 130, about 140, about 150, about 160, about 170, about 180, about 190, or about 200. In another embodiment of the invention, the retention time is about 30 seconds, about 1 min., about 10 min., about 20 min., about 30 min., about 1 hour, about 2 hours, about 3 hours, about 5 hours, about 8 hours, about 10 hours, about 15 hours, about 20 hours or about 24 hours. The heat treatment is preferably conducted at a pH of between about 3 and about 9; for example, the pH may be about 3, about 4, about 5, about 6, about 7, about 8 or about 9.

The alcohol may be separated from the fermentation broth or "beer" by distillation using conventional methods. As used herein, the term "distillation" also encompasses steam and vacuum stripping, provided that the conditions of the separation are harsh enough to denature cellulase enzyme as described herein.

The fermentation broth or beer that is sent to distillation is a dilute alcohol solution containing solids, including unconverted cellulose, and any components added during the fermentation to support growth of the microorganisms. Microorganisms are potentially present depending upon whether or not they are recycled during the fermentation. The beer is preferably degassed to remove carbon dioxide and then pumped through one or more distillation columns to separate the alcohol from the other components in the beer. The column(s) in the distillation unit is preferably operated in a continuous mode, although it should be understood that batch processes are also encompassed by the present invention. Furthermore, the column(s) may be operated at greater than atmospheric pressure, at less than atmospheric pressure or at atmospheric pressure. Heat for the distillation process may be added at one or more points either by direct steam injection or indirectly via heat exchangers. The distillation unit may contain one or more separate beer and rectifying columns. In this case, dilute beer is sent to the beer column where it is partially concentrated. From the beer column, the vapour goes to a rectification column for further purification. Alternatively, a distillation column is employed that comprises an integral enriching or rectification section. The remaining water may be removed from the vapour by a molecular sieve resin, by adsorption, or other methods familiar to those of skill in the art. The vapour may then be condensed and denatured.

An aqueous stream(s) remaining after distillation and containing solids, referred to herein as "still bottoms", is withdrawn from the bottom of one or more of the columns of the distillation unit. This stream contains unconverted cellulose. In addition, this stream may contain microorganisms, inorganic salts, unfermented sugars, organic salts and other impurities.

The distillation is carried out at sufficiently harsh conditions to denature bound cellulase enzyme. The distillation is preferably carried out at a temperature of between about 70° C. and about 200° C., more preferably between about 90° C. and about 180° C., or any temperature range therebetween, e.g. at temperatures, in ° C., of about 100, about 110, about 120, about 130, about 140, about 150, about 160, and about 170 at a pressure between about 2.0 psia and about 215 psia, or any pressure range therebetween. The retention time of the liquid stream which contains unhydrolyzed solids within the distillation unit is between about 0.05 and about 12 hours, or any time period therebetween. The temperature is measured at the bottom portion of a distillation column(s) from which still bottoms comprising cellulose are withdrawn, and the pressure is measured at the top portion of a distillation column(s). In one embodiment, the distillation is conducted at a temperature, in ° C. of about 70, about 80, about 90, about 100, about 110, about 120, about 130, about 140, about 150, about 170, about 180, about 190, or about 200° C. In another embodiment, the distillation is conducted at a pressure in psia of about 2.0, about 5.0, about 8.0, about 10.0, about 15.0, about 20, about 25, about 50, about 100, about 125, about 150, about 175, about 200, or about 215. In yet a further embodiment of the invention, the retention time of the liquid stream which contains unhydrolyzed solids within the distillation unit in hours, is about 0.25, about 0.30, about 0.35, about 0.40, about 0.45, about 0.50, about 0.60, about 0.70, about 0.80, about 0.90, about 1.0, about 1.25, about 1.5, about 1.75, about 2.0, about 2.5, about 3.0, about 4.0, about 5.0, about 6.0, about 7.0, about 8.0, about 9.0, about 10.0, about 11.0 or about 12.0.

The still bottoms stream is subsequently fed to a further cellulase hydrolysis. This may be carried out by feeding it to a downstream enzyme hydrolysis with the addition of fresh cellulase enzyme, or, alternatively, re-circulating at least a portion of the stream back to an upstream enzymatic hydrolysis. When the still bottoms stream is recycled, the unhydrolyzed cellulose becomes an additional substrate which proceeds to the cellulase hydrolysis, together with the pretreated feedstock fed to the process.

The suspended solids concentration of the still bottoms stream may be between 3 and 40% and will depend on whether the stream has been concentrated prior to further hydrolysis. For example, the solids concentration may be, in %, about 3, about 5, about 7, about 8, about 10, about 12, about 14, about 16, about 18, about 20, about 22, about 24, about 26, about 28, about 30, about 32, about 34, about 36, about 38 or about 40%. If the stream is to be concentrated, it may be subjected to any known solids-liquid separation, with the solids then sent to the further hydrolysis. According to this embodiment, the solids concentration will typically be between about 12 and about 40%, or any range therebetween. Examples of preferred solids-liquid separation techniques include evaporation, centrifugation, microfiltration, plate and frame filtration, crossflow filtration, pressure filtration and vacuum filtration. If the still bottoms stream is subjected to further hydrolysis without separation, it will typically have a solids concentration of between about 3 and about 10%.

Referring now to the embodiment shown in the drawings, FIG. 1 depicts a process flow diagram for producing ethanol from a lignocellulosic feedstock 102. The lignocellulosic feedstock 102 is optionally slurried in water and then subjected to pretreatment 104, which involves the addition of acid and steam, and reacting the lignocellulosic feedstock at a pH, temperature and duration of time to hydrolyze the hemicellulose component of the feedstock to the sugar monomers xylose, galactose, mannose and arabinose. After adjustment of the pH of the pretreated feedstock to between 4.5 and 5.5 with alkali, the feedstock is hydrolyzed in a first enzyme hydrolysis 106 with cellulase to produce a hydrolyzate slurry comprising glucose and unconverted cellulose. The hydrolyzate slurry is then fed to a first fermentation 108 to convert the glucose to ethanol with the yeast *Saccharomyces cerevisiae*.

The ethanol is then distilled in a first distillation 110 to produce a stream comprising concentrated ethanol and a still bottoms stream comprising unconverted cellulose, which is fed to a second cellulase hydrolysis 112 (also referred to as a downstream hydrolysis), where cellulase is added to the solids. After hydrolysis of the still bottoms stream in the second hydrolysis 112 or downstream hydrolysis, a hydrolyzate slurry comprising glucose is withdrawn and fed to a second fermentation 118 to produce ethanol and a second distillation 120 to recover the ethanol from the fermentation broth.

Figure 2:
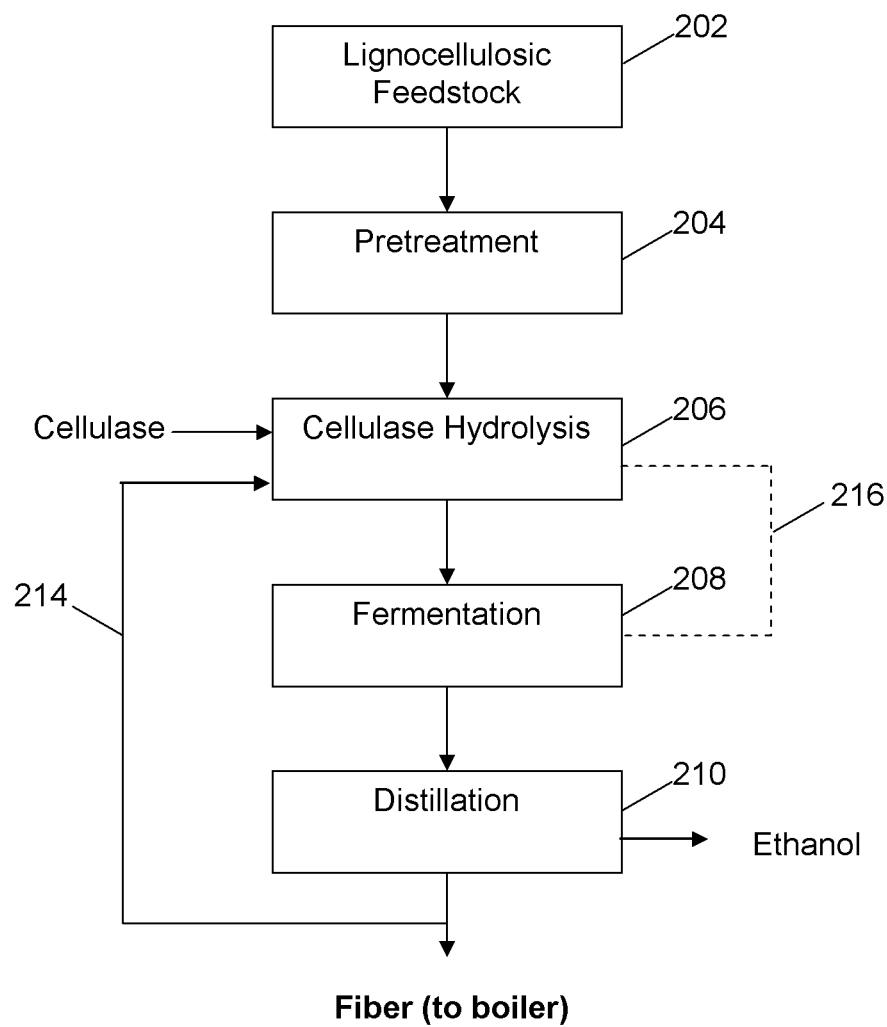

FIG. 2 shows an alternative embodiment in which a still bottoms stream 214 is introduced as the fed feed to the upstream cellulase hydrolysis 206. According to this embodiment, at least a portion of the unconverted cellulose remaining in the still bottoms is hydrolyzed to glucose with cellulase enzymes along with incoming pretreated feedstock from pretreatment 204. A hydrolyzate stream, containing glucose derived both from the pretreated feedstock and the recycled still bottoms, is then fermented 208 to produce ethanol, followed by distillation 210, as described previously. This embodiment is particularly advantageous in that it does not necessitate the inclusion of a second (downstream) hydrolysis system, fermentation and distillation system, which adds to the cost and complexity of the process.

Optionally, a portion of the fermentation broth comprising alcohol may be re-circulated back as a feed stream 216 to the enzymatic hydrolysis 206. By recycling this stream 216 to the hydrolysis 206, the ethanol concentration in the feed to the distillation 210 is at a sufficiently high level to substantially lower its cost of recovery. Furthermore, at this stage of the process, the cellulase enzyme has not been subjected to the harsh conditions of the distillation or steam stripping operations, and thus a portion of the cellulase enzyme will still be active. Therefore, by recycling stream 216, active cellulase enzyme remaining bound to the unconverted cellulose is re-introduced to hydrolysis 206.

Furthermore, it should be appreciated that, in the embodiment described in FIG. 1, a portion of the still bottoms stream 114 may be recycled back to the first cellulase hydrolysis 106. The balance of the still bottoms stream is sent to the second downstream cellulase hydrolysis 112.

Figure 5:
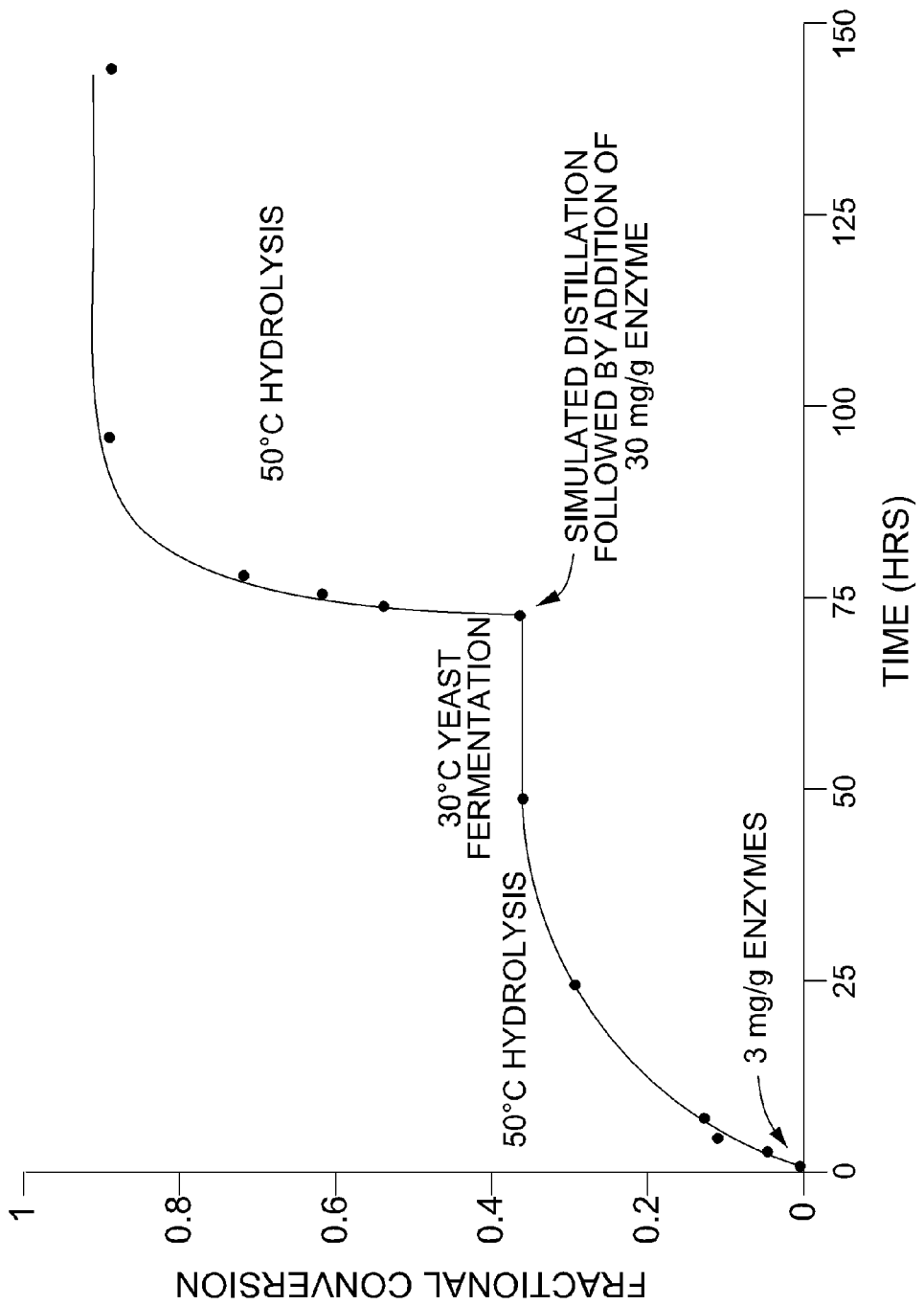
FIG. 5 and FIG. 6 are graphs which show the fractional cellulose conversion of a slurry of pretreated wheat straw in a pH 5 aqueous slurry. The cellulose conversion was measured throughout a first hydrolysis with cellulase enzyme, a fermentation of the glucose to ethanol by yeast, heating the slurry at 90° C. to simulate distillation, followed by a second hydrolysis with cellulase enzymes.
Figure 6:
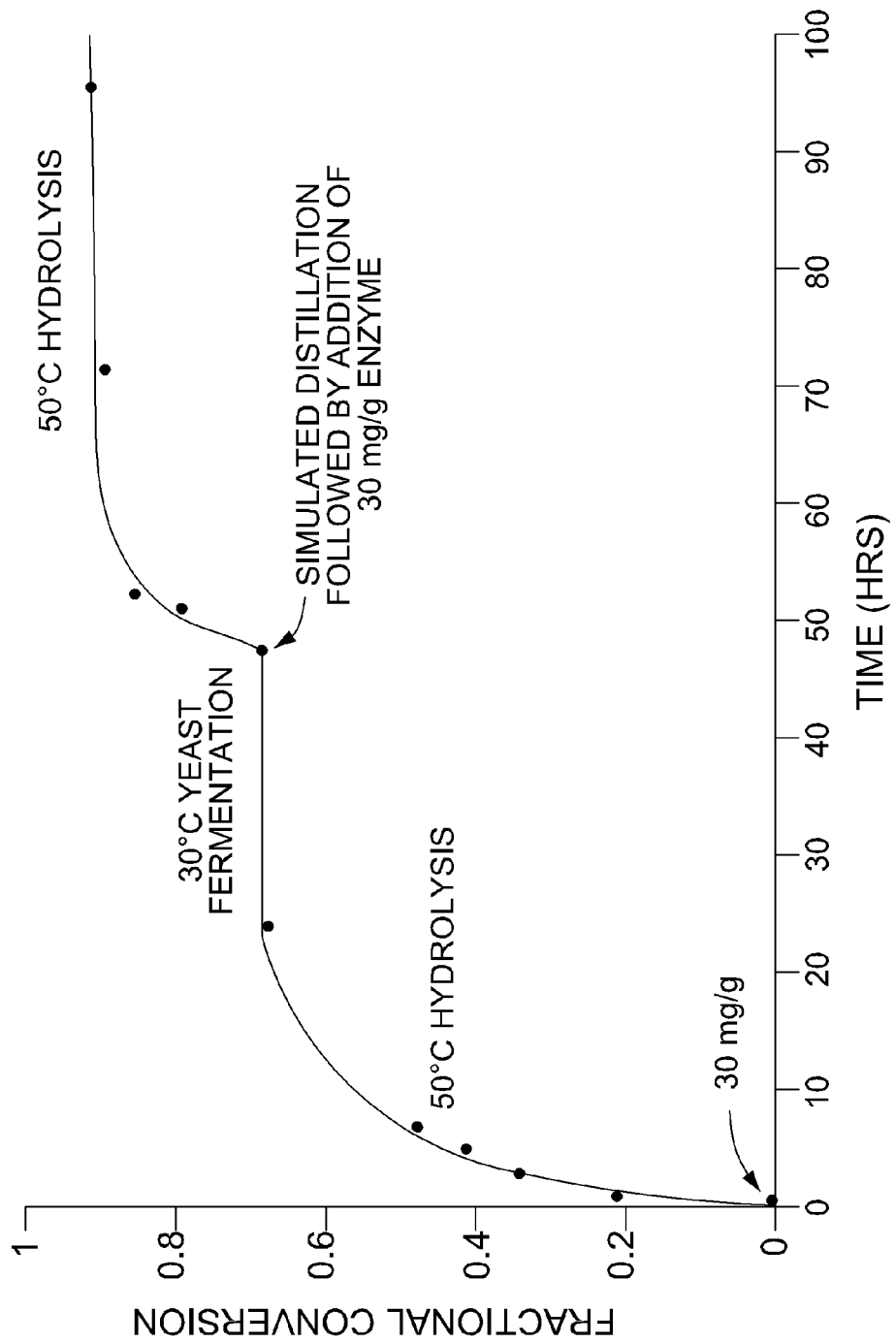

The unconverted cellulose remaining in the still bottoms stream is particularly amenable to the further enzymatic hydrolysis with cellulase enzymes. As shown in FIGS. 5 and 6, after heat denaturation to simulate distillation, a substantial increase in the fractional conversion of cellulose upon further cellulase hydrolysis is observed. Thus, by providing for a further hydrolysis of unhydrolyzed cellulose at this stage of the process, the amount of fermentable sugars obtained from the feedstock can be greatly enhanced, which, in turn increases the yield of ethanol or other fermentation products from the feedstock. It is believed that the increase in cellulose conversion is the result of the enzyme being denatured by the harsh conditions of the distillation (conducted between 70° C. and 200° C., for 0.05-12 hours). This produces a regenerated substrate surface which contains very little or no bound cellulase enzyme, and thus increases the number of sites available to the enzyme on the surface of the cellulose.

Figure 3:
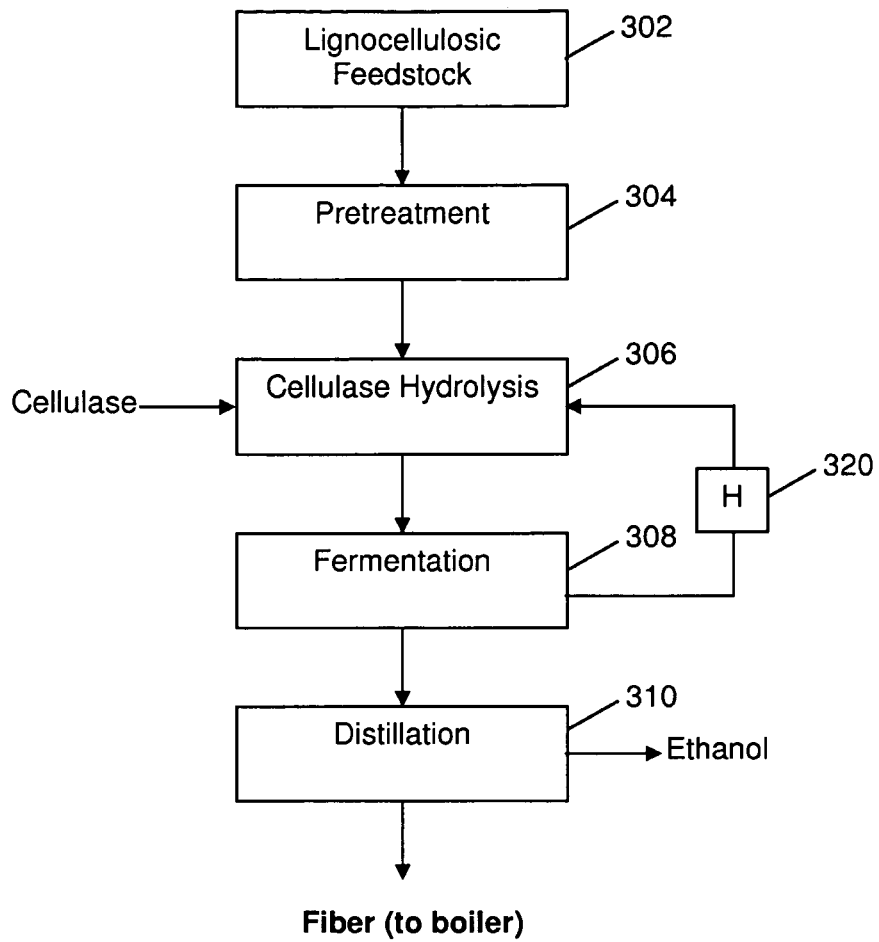

FIG. 3 shows another embodiment of the invention in which the fermentation broth comprising glucose is subjected to a processing step comprising a heat treatment. According to this embodiment, a portion of the fermentation broth comprising unhydrolyzed cellulose resulting from fermentation 308 is withdrawn, subjected to a heat treatment 320 and then recycled to the cellulase hydrolysis 306. The balance of the stream is then submitted to distillation 310 to obtain concentrated ethanol.

Figure 4:
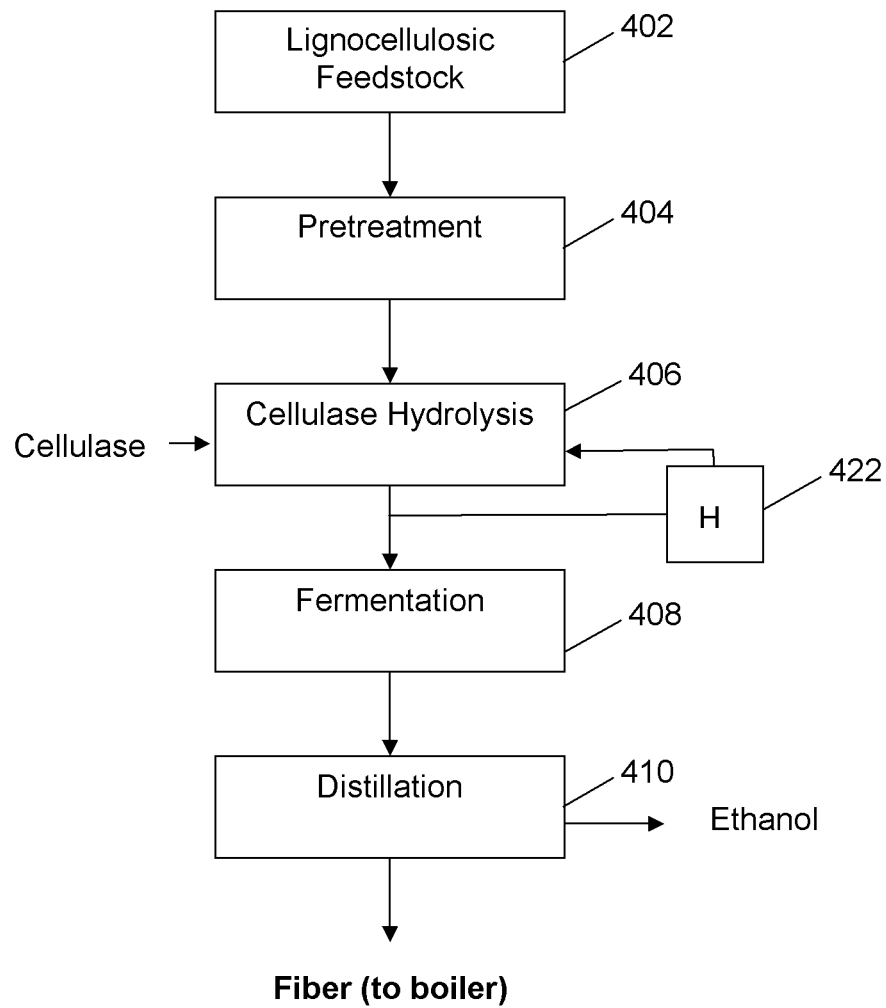

FIG. 4 shows yet another embodiment of the invention in which the hydrolyzate slurry resulting from cellulase hydrolysis 406 is subjected to heat treatment 422 and then re-circulated back to the cellulase hydrolysis 406. The balance of the stream is then submitted to fermentation 408 to obtain ethanol, followed by distillation 410 to recover the ethanol.

It should be appreciated that thermostable cellulase enzymes may also be employed in the hydrolysis. However, when thermostable enzymes are utilized, they must be exposed to temperatures that are high enough to ensure that the enzyme is denatured (i.e., typically greater than about 90° C.).

Although the use of a heat denaturation step has been described, it should be appreciated that the enzyme bound to the cellulose may be denatured by changes in pH, protease treatment, the addition of oxidizing chemicals, or other chemicals that inactivate enzyme.

The present invention will be further illustrated in the following examples. However, it is to be understood that these examples are for illustrative purposes only, and should not be used to limit the scope of the present invention in any manner.

EXAMPLES

Example 1

Enzymatic Hydrolysis after Simulated Distillation

Wheat straw was pretreated at 185° C., pH 1.0 with 1 wt % sulfuric acid in a manner consistent with Foody, U.S. Pat. No. 4,461,648 After pretreatment, the straw was washed with water and stored in a 4° C. refrigerator. The washed, pretreated wheat straw was hydrolyzed with cellulase enzymes made by a strain of *Trichoderma reesei* that was genetically modified to overexpress β-glucosidase and cultivated in a submerged culture fermentation, as described by White and Hindle, (U.S. Pat. No. 6,015,703). The stock of enzyme was concentrated by ultrafiltration to a final concentration of 133 Filter Paper Units per mL (165 g protein/L) and stored refrigerated. The cellulose hydrolysis was carried out in 50 mM $KH_2PO_4$ buffer, pH 5.0, in a total volume of 50 mL in screw top flasks at a cellulose concentration of 2.53%. The cellulase enzyme was added at a dose of 3 mg protein per gram cellulose (3 mg/g), and the hydrolysis was conducted at 50° C. with shaking at 250 rpm for 48 hours prior to fermentation.

The flasks were then cooled to 30° C. and Superstart™ (obtained from Ethanol Technology Lallemand) dry *Saccharomyces cerevisiae* yeast was added to the hydrolysis slurry at a concentration of 1.5 g/L. After addition of the yeast, the flasks were sealed and incubated in a 30° C. shaker and shaken at 200-250 rpm for 24 hours to allow fermentation.

Samples were collected throughout the hydrolysis runs and used to measure the glucose and the ethanol concentrations. These were measured by HPLC using an Aminex™ column with a refractive index (RI) detector to separate the sugars, organic acids and alcohols. For example, to calculate the concentration of ethanol in the samples, the chromatograms of the standard and samples were used. The concentration is measured using the areas for the peaks with the same retention time as the standard are as follows:

Concentration of sample=area(sample)/area(standard)
*dilution factor*concentration of standard.

Once the fermentation process was complete, the flasks were submerged in boiling water for 40 minutes to simulate temperatures which would be employed during a typical distillation process. The temperature of the flask content was monitored and was roughly 90° C. throughout the entire heating process. At the end of the simulated distillation, the flasks were cooled to 50° C. and 30 mg/g of fresh cellulase enzyme was added to the slurry. The flasks were then placed back in the 50° C. shaker and shaken at 250 rpm until the end of the run. Several samples were collected throughout these hydrolyses. The glucose and ethanol concentrations in the samples were measured as set forth above.

The fractional cellulose conversion is determined by dividing the glucose concentration by that which would be present if all of the cellulose were concerted to glucose. The calculation takes into account the molecule of water of hydration of the cellulose with each molecule of glucose made.

FIG. 5 is a graph which shows the fractional conversion of cellulose throughout the first cellulase hydrolysis, the fermentation, the simulated distillation and the second cellulase hydrolysis. As can be seen from the FIG. 5, the second hydrolysis conducted after the simulated distillation at 72 hours resulted in a substantial increase in the fractional conversion of cellulose. These results thus demonstrate that a further hydrolysis of still bottoms remaining after a distillation operation could be employed to enhance the yield of fermentable sugar from a lignocellulosic feedstock. It is believed that the substantial increase in cellulose conversion observed during the continued cellulase hydrolysis is due to removal of the cellulase from the cellulose during the simulated distillation, thereby creating new sites on the substrate for the enzyme.

The hydrolysis, fermentation, simulated distillation and continued hydrolysis were repeated in a second run under the reaction conditions set forth above, but with the following differences: the initial hydrolysis was conducted for only 24 hours, rather than 48 hours; the initial cellulase enzyme dosage was 30 mg/g, rather than 3 mg/g; and the cellulose concentration of the slurry was 6.01%, rather than 2.53%.

The cellulose fractional conversion of this second run is shown in FIG. 6. As can be seen from FIG. 6, the addition of 30 mg/g cellulase after simulated distillation at 48 hours also resulted in enhanced conversion of cellulose. Thus, FIG. 6 exhibits a similar trend to that observed in FIG. 5, namely an enhancement in the fractional conversion of cellulose after simulated distillation.

Example 2

Comparative Example without Simulated Distillation

In order to determine whether or not the enhanced hydrolysis observed was due to simulated distillation, the hydrolysis was conducted as in the first run of Example 1 (See FIG. 2A), but the fermentation and simulated distillation were omitted. Furthermore, the wheat straw contained 2.5% cellulose and fresh cellulase enzyme at a dose of 30 mg/g was added at 24 hours.

Figure 7:
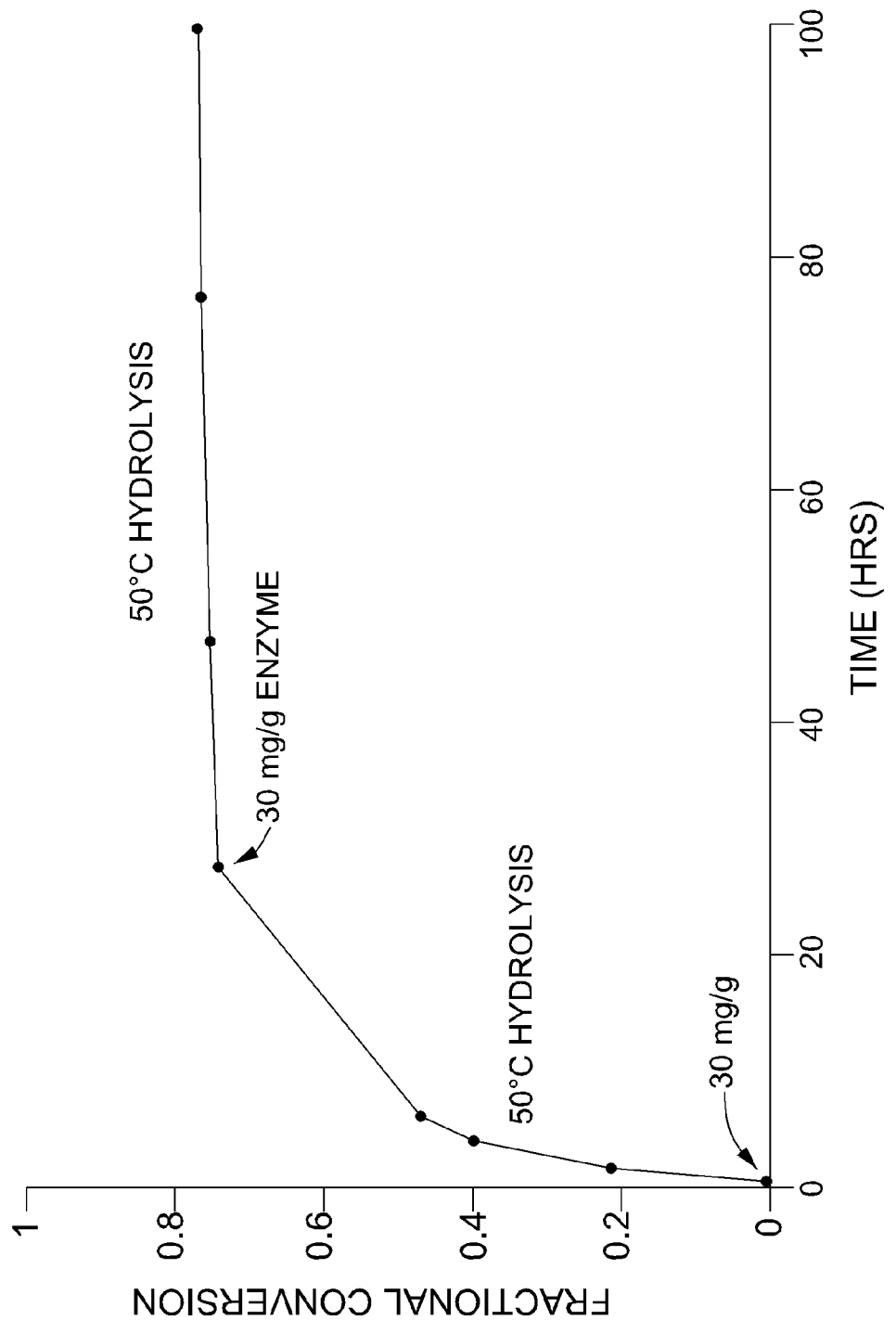
FIG. 7 is a graph which shows the fractional cellulose conversion of a slurry of pretreated wheat straw in pH 5 aqueous slurry without simulated distillation. The cellulose conversion was measured throughout a first hydrolysis with cellulase enzyme, followed by a second hydrolysis with cellulase enzymes. Cellulase was added at the beginning of the hydrolysis at 30 mg/g and the wheat straw slurry contained 2.5% cellulose. Fresh cellulase enzyme at a dose of 30 mg/g was added at 24 hours.

As shown in FIG. 7, when 30 mg/g of fresh enzyme was added to the flask at 24 hours, the cellulose conversion did not improve significantly. When comparing FIG. 7 to FIGS. 5 and 6 it can be seen that the simulated distillation did, in fact, significantly improve the cellulose hydrolysis.

Example 3

Enzymatic Hydrolysis after Distillation

Wheat straw 102 was pretreated 104 at 210° C., pH 1.55 with 0.25 wt % sulfuric acid in a manner consistent with Foody, U.S. Pat. No. 4,461,648 (the entire contents of which is incorporated herein by reference) according to the process flow diagram shown in FIG. 1. After pretreatment, the straw was dewatered by an Alfa Laval decanter centrifuge to 25% solids content. The decanter cake was combined with centrate to a concentration of 13% solids, and then pumped into a hydrolysis mix tank of volume 5000 liters.

In the mix tank, the slurry was cooled to 50° C. The pH was adjusted to 5.0 by adding 30% ammonium hydroxide solution. Cellulase enzyme was then added to the slurry. The cellulase was made by a strain of *Trichoderma reesei* that was genetically modified to overexpress beta-glucosidase and cultivated in a submerged culture fermentation, as described by White and Hindle, U.S. Pat. No. 6,015,703 (the entire content of which is incorporated herein by reference). The stock of enzyme was concentrated by ultrafiltration to a final concentration of 133 Filter Paper Units per ml (165 g protein/ L) and stored refrigerated. The cellulase enzyme was added at a dosage of 30 mg protein per gram cellulose (30 mg/g), which vessel 106 has a volume of 150,000 liters. The mix tank is operated continuously with a residence time of 1 hour.

Slurry from the mix tank was fed to the main hydrolysis tank, which has a volume of 150,000 liters. Slurry was fed until the vessel was full. The hydrolysis was conducted at 50° C. with agitation at 12-15 RPM for 96 hours. At this point, the final glucose concentration was 75 g/L which corresponds to a cellulose conversion of 89%.

At this point, the hydrolysis slurry was pumped through a heat exchanger to cool it down to 30° C. The cooled slurry was then pumped onward into one of three fermentation vessels 108 of working volume 68,000 liters. At any one time, one vessel was being filled, one was running, and one was being emptied. Superstart™ (obtained from Ethanol Technology Lallemand) dry *Saccharomyces cerevisiae* yeast was added to the fermenter slurry at a concentration of 0.2 g/L. After addition of the yeast, the vessel was mixed for the 24 hr duration of the fermentation. The final ethanol concentration was 34 g/L.

Once the fermentation was complete, the fermentation broth was pumped to the distillation column 110 and distilled to recover the ethanol. Distillation was carried out in a continuous system with the bottoms temperature of 121° C., the reboiler at 123° C., and the overheads at 88° C. The still bottoms are essentially free of ethanol. The 10 minutes of liquid residence time in the distillation system was sufficient to denature the cellulase enzyme.

The still bottoms were concentrated to 46% solids on a filter press.

The filter press cake solids consisted of 11.9% cellulose. A portion of this cake was sent to a second hydrolysis 112. This was carried out by suspending the cake in a 250 ml shake flask in 50 mM sodium citrate buffer (pH 5.0) to a solids concentration of 10%. Cellulase enzyme was added at a dosage of 30 mg protein/g cellulose. The flask was shaken for 24 hr at 50° C. and sampled periodically. After 24 hr, the glucose concentration in the flask was 8.5 g/L which represents an overall conversion of the initial cellulose in the first hydrolysis to glucose of 96.1%. The broth containing glucose was sent for fermentation 118 and second distillation 120.

What is claimed is:

1. A process for increasing the hydrolysis of cellulose in the production of alcohol from a lignocellulosic feedstock, comprising the steps of:
   (i) pretreating a lignocellulosic feedstock under conditions to produce a composition comprising a pretreated lignocellulosic feedstock having a disrupted fiber structure and increased accessibility of the feedstock to being hydrolyzed;
   (ii) enzymatically hydrolyzing the pretreated lignocellulosic feedstock with cellulase enzymes to produce a hydrolyzate slurry comprising glucose and unhydrolyzed cellulose;
   (iii) fermenting said hydrolyzate slurry to produce a fermentation broth comprising alcohol and unhydrolyzed cellulose;
   (iv) separating the alcohol from the fermentation broth by distillation to obtain a stream comprising concentrated alcohol and a still bottoms stream comprising the unhydrolyzed cellulose and the cellulase enzymes, said distillation resulting in heat treatment of the unhydrolyzed cellulose, which heat treatment is conducted at a temperature between 70 and 200° C. so as to denature the cellulase enzymes; and
   (v) further hydrolyzing at least a portion of the still bottoms stream with cellulase enzymes to convert at least a portion of the unhydrolyzed cellulose present in said still bottoms stream to glucose, thereby increasing cellulose hydrolysis.

2. The process according to claim 1, wherein the step (v) of further hydrolyzing comprises recycling at least a portion of the still bottoms stream back to step (ii).

3. The process according to claim 1, wherein the step (v) of further hydrolyzing comprises introducing at least a portion of the still bottoms stream to a downstream hydrolysis reactor.

4. The process according to claim 1, wherein the step (ii) of enzymatically hydrolyzing the pretreated lignocellulosic feedstock and the step (iii) of fermenting said hydrolyzate slurry are carried out in separate reactors.

5. The process according to claim 1, wherein the step (i) of pretreatment is carried out with a pH adjustant.

6. The process according to claim 5, wherein the pH adjustant is acid or alkali.

7. The process according to claim 1, wherein the step (ii) of enzymatically hydrolyzing the pretreated lignocellulosic feedstock is carried out in a hydrolysis system comprising at least one hydrolysis reactor selected from the group consisting of agitated tanks, unmixed tanks, agitated towers and unmixed towers.

8. The process according to claim 1, wherein the step (ii) of enzymatically hydrolyzing is a batch process.

9. The process according to claim 1, wherein the alcohol produced in the step (iii) of fermenting is ethanol or butanol.

10. The process according to claim 9, wherein the distillation step (iv) is carried out with a slurry retention time of between about 0.05 and about 12 hours.

11. The process according to claim 10, wherein the temperatures of the distillation step (iv) are between about 70° C. and about 180° C.

12. The process according to claim 1, further comprising recycling at least a portion of the fermentation broth back to step (ii).

13. The process according to claim 1, wherein the concentrated still bottoms stream has a solids concentration of between 12 and 40% by weight.

14. A process for improving cellulose hydrolysis in the production of ethanol from a lignocellulosic feedstock, comprising the steps of:
   (i) pretreating a lignocellulosic feedstock under conditions to produce a composition comprising a pretreated lignocellulosic feedstock having a disrupted fiber structure and increased accessibility of the feedstock to being hydrolyzed;
   (ii) enzymatically hydrolyzing the pretreated lignocellulosic feedstock with cellulase enzymes to produce a hydrolyzate slurry comprising glucose and unhydrolyzed cellulose;
   (iii) fermenting said hydrolyzate slurry to produce a fermentation broth comprising ethanol;
   (iv) separating the ethanol from the fermentation broth by distillation to obtain a stream comprising concentrated ethanol and a remaining still bottoms stream comprising unhydrolyzed cellulose and the cellulase enzymes, said distillation resulting in heat treatment of the unhydrolyzed cellulose, which heat treatment is conducted at temperatures between 70 and 200° C. so as to denature the cellulase enzymes;
   (v) further hydrolyzing at least a portion of the still bottoms stream with cellulase enzymes to convert the unhydrolyzed cellulose to glucose by recycling at least a portion of the still bottoms stream back to step (ii), thereby increasing cellulose hydrolysis; and
   (vi) subsequent to the distillation, obtaining a concentrated ethanol product.

15. The process according to claim 14, wherein the concentrated still bottoms stream has a solids concentration of between 12 and 40% by weight.

16. A process for producing glucose from a lignocellulosic feedstock, comprising the steps of:
   (i) pretreating the lignocellulosic feedstock under conditions to produce a pretreated lignocellulosic feedstock having disrupted fiber structure and increased accessibility of the lignocellulosic feedstock to being hydrolyzed;
   (ii) enzymatically hydrolyzing the pretreated lignocellulosic feedstock with cellulase enzymes to produce a hydrolyzate slurry comprising glucose and unhydrolyzed cellulose and fermenting the glucose to produce a fermentation broth comprising alcohol;
   (iii) obtaining at least a portion of the hydrolyzate slurry comprising the unhydrolyzed cellulose;
   (iv) subjecting at least a portion of said hydrolyzate slurry to a processing step comprising exposing the unhydrolyzed cellulose to a temperature of between about 70° C. and about 250° C., thereby producing a hydrolyzate slurry comprising heat-treated unhydrolyzed cellulose; and (v) further hydrolyzing the heat-treated unhydrolyzed cellulose in said hydrolyzate slurry with cellulase enzymes to convert at least a portion of the unhydrolyzed cellulose to glucose.

17. The process according to claim 16, wherein the pretreatment step (i) is carried out with a pH alterant.

18. The process according to claim 17, wherein the pH alterant is acid or alkali.

* * * * *